United States Patent [19]
Kaelin, Jr. et al.

[11] Patent Number: 5,981,723
[45] Date of Patent: *Nov. 9, 1999

[54] RETINOBLASTOMA-ASSOCIATED PROTEIN 1 CDNA

[75] Inventors: William G. Kaelin, Jr., Boston; Erik Flemington, Brookline; James A. DeCaprio, Wellesley; William Sellers; David M. Livingston, both of Brookline, all of Mass.

[73] Assignee: Dana-Farber Cancer Institute, Boston, Mass.

[*] Notice: This patent is subject to a terminal disclaimer.

[21] Appl. No.: 08/462,174

[22] Filed: Jun. 5, 1995

Related U.S. Application Data

[62] Division of application No. 07/882,711, May 13, 1992, Pat. No. 5,759,803.

[51] Int. Cl.$^6$ ................................................ C12N 15/12
[52] U.S. Cl. ................... 536/23.5; 536/24.31; 435/320.1
[58] Field of Search ............................... 536/23.5, 24.31; 435/320.1

[56] References Cited

FOREIGN PATENT DOCUMENTS

WO 89/06703   7/1989   WIPO.

OTHER PUBLICATIONS

Yee et al., "Promoter Interaction of the E1A–Inducible Factor E2F and Its Potential Role in the Formation of a Multi–Component Complex," *The EMBO Journal*, vol. 6, No. 7, pp. 2061–2068, 1987.

Defeo–Jones, et al., "Cloning of cDNAs for Cellular Proteins That Bind to the Retinoblastoma Gene Product," *Nature*, vol. 352, pp. 251–254, Jul. 18, 1991.

Kaelin, et al., "Identification of Cellular Proteins That Can Interact Specifically with the T/E1A–Binding Region of the Retinoblastoma Gene Product," *Cell*, vol. 64, pp. 521–532, Feb. 8, 1991.

Huang, et al., "Suppression of the Neoplastic Phenotype by Replacement of the RB Gene in Human Cancer Cells," *Science*, vol. 242, pp. 1563–1566, Dec. 16, 1988.

Hu, et al., "The Regions of the Retinoblastoma Protein Needed for Binding to Adenovirus E1A or SV40 Large T Antigen are Common Sites for Mutations,"*EMBO J.*, vol. 9, pp. 1147–1155, 1990.

Huang, et al., "Two Distinct and Frequently Mutated Regions of Retinoblastoma Protein Are Required for Binding to SV40 T Antigen," *EMBO J.*, vol. 9, pp. 1815–1822, 1990.

Kaelin, et al., "Definition of the Minimal Simian Virus 40 Large T Antigen–And Adenovirus E1A–Binding Domain in the Retinoblastoma Gene Product," *Mol. and Cel. Biol.*, vol. 10, pp. 3761–ff, Jul. 1990.

Huang, et al., "A Cellular Protein that Competes with SV40 T Antigen for Binding to the Retinoblastoma Gene Product", *Nature*, vol. 350, pp. 160–162, Mar. 14, 1991.

Bandara, et al., "Adenovirus E1a Prevents Retinoblastoma Gene Product from Complexing with a Cellular Transcription Factor," *Nature*, vol. 351, pp. 494–497, Jun. 6, 1991.

Chellappan, et al., "The E2F Transcription Factor is a Cellular Target for the RB Protein," *Cell*, vol. 65, pp. 1053, 1061, Jun. 14, 1991.

Bagchi, et al., "The Retinoblastoma Protein Copurifies with E2F–I, and E1A–Regulated Inhibitor of the Transcription Factor E2F", *Cell*, vol. 65, pp. 1063–1072, Jun. 14, 1991.

Chittenden, et al., "The T/E1A–Binding Domain of the Retinoblastoma Product Can Interact Selectively with a Sequence–Specific DNA–Binding Protein", *Cell*, vol. 65, pp. 1073–1082, Jun. 14, 1991.

Yee, A.S., et al., *Mol. Cell. Biol.*, 9(2):578–85 (1989).

Gustin, M.C., et al., *Science*, 233:1195–97 (1986).

Aruffo, A., et al., *Proc. Natl. Acad. Sci.*, 84:8573–77 (1987).

Aebersold, R.H., et al., *J. Biol. Chem.*, 261:4229–38 (1986).

*Primary Examiner*—Anthony C. Caputa
*Assistant Examiner*—Robert C. Hayes
*Attorney, Agent, or Firm*—Ronald I. Eisenstein; David S. Resnick; Nixon Peabody LLP

[57] ABSTRACT

We have discovered a nuclear protein in normal human cells, "retinoblastoma-associated protein 1" ("RBAP-1") that binds directly to the retinoblastoma protein pocket of the underphosphorylated form of the retinoblastoma protein ("RB") and does not bind to phosphorylated RB or to RB with inactivating mutations. The translated RBAP-1 sequence does not resemble other proteins whose sequences are known, and RBAP-1 does not contain a sequence homologous to the transforming element common to viral proteins that bind to the RB pocket. RBAP-1 and the E2F transcription activity have similar DNA-binding specificities and can bind to at least some of the same proteins, such as RB and E4.

1 Claim, 2 Drawing Sheets

FIG. 1A

```
1561 TAGGAGGCTGAGCAAGCCAGGAAGGGAAGGAGTCTGTGTGTGGTGTGTATGCATGAGCCTACACCCACGTGTGTACCGGGGTGAATGTGTGTGAGCATGTGTGTGCATGTACCG
1681 GGGAATGAAGGTGAACATACACCTCTGTGTGCACTGTGCAGACACGCCCCCAGTGTGTCCACATGTGTGCATGAGTCCATGTGTGCGCGTGCGGGCCTCTAACTGCACTTCGGCCT
1801 TTTGCTCTGGGGTCCACAAGGCCCAGGGCAGTGCCTCTGCCTCTCCCAGAATCTGGTGCTCTGACCAGGCCAGTGGGGAGGCTTTGGCTGCTGGGCGTTGAGGACGTGAGAGCACTTCTGT
1921 CTTAAAGGTTTTTCTGATTGAAGCTTAATGGAGGTTATTTATTTATTCATGAGCCTCTCTTTGTGAGCCTGTTATTTATTGGAAGTTTGATATACCCAACTCCC
2041 TCTACCCTTGAGCAAGGGCAGGGGTCCAGGGGTCCCCATACTGAAGAACTGAGGCCTGGTGATTATTATTGGAAAGTGAGGGAGGAGACAGACTGACAGC
2161 CATGGGGTGGTCAGATGGTGGGGTGGGCCCTCTCCAGGGGGCCCAGTTCAGGGCCCAGCTGCCCCCAGATGGATATGAGATGGGAGAGTGAGTGGGGACCTTCACTGATGTGGCAG
2281 GAGGGGTGGTGAAGGCCTCCCCAGCCAGCCCTGTGTCCTGAAGCGCCTGCCTCCCCACCTGCTCGCCCCCCTCCAATCTGCACTTTGATTTGCTTCCTAAC
2401 AGCTCTGTTCCCTCCTGCTTTGGTTTAATAAATATTTTGATGACGTTAAAAAAAA
```

FIG. 1B

RETINOBLASTOMA-ASSOCIATED PROTEIN 1 CDNA

This is a divisional of application Ser. No. 07/882,711 filed on May 13, 1992, now U.S. Pat. No. 5,759,803.

BACKGROUND OF THE INVENTION

This invention was made in the course of work supported in part by U.S. Government funds, and the government has certain rights in the invention.

This invention relates to tumor suppressor genes.

The human retinoblastoma gene ("RB-1") is considered to be the prototype of a class of genes, generally known as "tumor suppressor genes", thought to be involved in suppressing neoplastic growth. Mutations in the retinoblastoma gene and dysfunction of its product have been implicated in the pathogenesis of a wide range of human tumors other than retinoblastomas, including bladder, breast, and small cell lung carcinomas, osteosarcomas, and soft tissue sarcomas. Furthermore, in cell populations where both copies of RB-1 are mutated, introduction of a wild-type copy of the gene can lead to a decrease in the growth rate or in the tumorigenicity of the cells expressing the exogenous gene (Huang et al., 1988, *Science*, Vol. 242, pp. 1563–1566). The retinoblastoma gene product, "RB", is believed to regulate cell growth, although the manner in which it does so is not well understood.

Several viral transforming proteins, the adenovirus E1A protein ("E1A"), the simian virus large T antigen ("T"), and the human papilloma virus E7 protein ("E7"), bind specifically to RB. The binding of the viral proteins to RB has been mapped to a region of RB termed the "pocket" (Hu et al., 1990, *EMBO J.*, Vol. 9, pp. 1147–1155; Kaelin et al., 1990, *Mol. Cel. Biol.*, Vol. 10, pp 3761–3769; Huang et al., 1990, *EMBO J.*, Vol. 9, pp. 1815–1822). The viral proteins share a short, homologous, colinear, transforming element, having at its core the amino acid sequence LXCXE, that is capable of binding to the RB pocket. A synthetic peptide of this viral element is capable of binding to the RB pocket and when bound blocks the binding of viral proteins to the RB pocket.

Analysis of RB throughout the cell cycle has demonstrated that it is phosphorylated and dephosphorylated at specific stages of the cell cycle. RB is non-phosphorylated, or "underphosphorylated", in the G0 and G1 phases and becomes phosphorylated at the start of S phase, the G1/S boundary, and remains phosphorylated throughout S phase, G2 and early mitosis (Buchkovich et al., 1989, *Cell*, Vol. 58, pp. 1097–1105; Chen et al., 1989, *Cell*, Vol. 58, pp. 1193–1198; DeCaprio et al., 1989, *Cell*, Vol. 58, pp. 1085–1095; Mihara et al., 1989, *Science*, Vol. 246, pp. 1300–1303; Xu et al., 1989, *Oncogene*, Vol. 4, pp. 807–812). In terminally differentiated cells and cells that are induced to terminally differentiate, RB is underphosphorylated (Mihara et al., 1989; Furukawa et al., 1990, *Proc. Natl. Acad. Sci. USA*, Vol. 87, pp. 2770–2774). Interaction of the viral transforming proteins with RB is cell-cycle regulated. For example, T does not bind to the phosphorylated form of RB (Ludlow et al. 1989, *Cell*, Vol. 56, pp. 57–65), suggesting that some of the growth suppressor functions of RB may be carried out by the underphosphorylated form of RB. The interaction of the viral transforming proteins with RB at specific stages of the cell cycle further supports the proposal that RB is involved in the pathogenesis of some human cancers.

SUMMARY OF THE INVENTION

We have discovered a nuclear protein in normal human cells, here termed "retinoblastoma-associated protein 1" ("RBAP-1") that, based on in vitro evidence, binds directly to the RB pocket of the underphosphorylated form of RB and does not bind to phosphorylated RB or to RB with inactivating mutations. The direct binding of RBAP-1 to RB suggests that RBAP-1 is involved in the RB signal transduction pathway.

We have fully sequenced a near full length clone of RBAP-1 encoding DNA ("RBAP-1"), and deduced the RBAP-1 amino acid sequence. A search of DNA sequence data bases reveals that RBAP-1 does not resemble other proteins whose DNA sequences are known. The deduced amino acid sequence of RBAP-1 also reveals that RBAP-1 does not contain a colinear sequence, LXCXE, homologous to the transforming element common to viral proteins that bind to RB, although it appears to bind to the same region of RB as do the viral transforming elements.

Analysis of RBAP-1 gene expression in cell culture demonstrated that RBAP-1 is expressed primarily during S phase of the cell cycle. RB becomes phosphorylated at the beginning S phase and we propose that RBAP-1 carries out a function related to the entry into, or traversal of, S phase by the cells.

Analysis of the DNA-binding properties of RBAP-1 has demonstrated that RBAP-1 binds to a DNA sequence that is also bound by cellular extracts that contain an activity known as E2F. E2F activity was originally described as an E1A-targeted component of the functional transcription complex of the adenovirus promoter and was later shown to be normally complexed to cellular proteins in most cell types. E2F has been functionally defined as a transcription factor that is a DNA-binding protein, and more recently has been shown to be a cellular target of RB (Bandara et al., 1991, *Nature*, Vol. 351, pp. 494–497; Chellappan et al., 1991, *Cell*, Vol 65, pp. 1053–1061; Bagchi et al., 1991, *Cell*, Vol. 65, pp. 1063–1072; Chittenden et al., 1991, *Cell*, Vol. 65, pp. 1073–1082). Also, E2F activity containing extracts have been shown to bind to the RB pocket, and this protein complex can be disrupted by E1A or E7. Interestingly, the RB bound E2F activity can recognize more than one DNA sequence (Chittenden et al., 1991). The binding of more than one DNA sequence by the E2F activity suggests that E2F may be a family of proteins.

In one general aspect the invention features a portion of a normal human nuclear protein that is capable of binding to the RB pocket.

In preferred embodiments the human nuclear protein is RBAP-1, having the sequence shown in FIG. 1. In other preferred embodiments RBAP-1 is synthesized in vitro using an RBAP-1 encoding DNA, or is made in vivo using an RBAP-1 encoding DNA or using the RBAP-1 gene. In some embodiments the portion of the human nuclear protein is the RB pocket binding portion of RBAP-1, comprising the nucleotide sequence 1191–1397 as shown in FIG. 1, or may be some other portion, and may be the entire RBAP-1 protein.

In another general aspect, the invention features a RBAP-1 encoding DNA. In preferred embodiments the RBAP-1 encoding DNA includes the nucleotide sequence shown in FIG. 1. In some embodiments the invention features a vector containing a portion of the RBAP-1 encoding DNA and may contain the entire RBAP-1 encoding DNA.

In another general aspect the invention features a vector containing a RBAP-1 gene.

In another general aspect, the invention features a method for diagnosing a condition of tumorigenicity in a subject, including the steps of obtaining a tissue sample from a subject and detecting the presence of non-wildtype RBAP-1 encoding gene in the sample, or detecting alterations in the expression of wildtype RBAP-1 encoding gene in the sample. "Alteration of expression" as used herein includes an absence of expression, or a substantially decreased expression, or an overexpression of the gene.

In another general aspect, the invention features a nucleic acid probe complementary to a portion of a RBAP-1 gene. The complementary nucleic acid probe, as used herein, can be complementary to any portion of a RBAP-1 gene including sense and anti-sense strands of the gene, and including coding and non-coding sequences.

In another general aspect, the invention features a ligand capable of binding to the RBAP-1 protein. In preferred embodiments, the ligand can bind to the RBAP-1 protein or to an RBAP-1/RB protein complex. The ligand can be a protein other than RB, a fusion protein, a polypeptide, or a small molecule. "Small molecule", as that term is used herein, means a chemical compound, a peptide, an oligonucleotide, having a sequence other than the sequences known to be bound by the E2F activity, or a natural product. Preferably the small molecule is a therapeutically deliverable substance.

In another general aspect, the invention features a ligand that is capable of altering the activation of a gene by RBAP-1. The ligand may alter gene activation by RBAP-1 by decreasing, the affinity of RBAP-1 for the specific DNA site, or decreasing, RBAP-1 transactivation of the promoter that is downstream from the DNA binding site.

In another general aspect, the invention features a ligand that is capable of disrupting the interaction of a viral transforming protein and RB, while not disrupting the interaction of RBAP-1 and RB.

In another general aspect the invention features methods for assaying for a ligand that is capable of disrupting the interaction of a viral transforming protein and RB, while not disrupting the interaction of RBAP-1 and RB. In one aspect the method comprises the steps of: immobilizing RB on a solid support; contacting the ligand and a viral transforming protein with the immobilized RB and separately contacting the ligand and RBAP-1, or a RB binding portion of RBAP-1; determining binding of the viral protein to RB and of RBAP-1 to RB in the presence of the ligand.

In another aspect the method comprises the steps of: transforming a first cell with vectors containing a reporter gene having an activatible promoter, and containing DNA encoding RB and RBAP-1 where one of the potential binding partners is fused to a transactivating domain and the other is fused to a site specific DNA binding domain; transforming a second cell with vectors containing a reporter gene having an activatible promoter, and containing DNA encoding RB and one viral transforming protein where one of the potential binding partners is fused to a transactivating domain and the other is fused to a site specific DNA binding domain; culturing the transformed cells in the presence of a ligand and determining the expression of the reporter gene. A preferred "cell" is a cultured eukaryotic cell, such as a yeast, for example S. cerevisiae, or a mammalian cell. An "activatible promoter", as used herein, is a promoter having a sequence specific binding site upstream of the transcriptional start site that is activated by the binding of a sequence specific DNA binding domain to the specific site and the proximity of a transactivating domain to the DNA binding domain. Each of these domains is fused to one protein of a pair that can interact to form a protein-protein complex and thus the domains are brought into the proximity required to activate transcription from the gene.

In another aspect the method comprises the steps of: transforming a mammalian cell expressing a viral transforming protein with vectors containing a reporter gene having an activatible promoter, and containing DNA encoding RB and RBAP-1 where one of the potential binding partners is fused to a transactivating domain and the other is fused to a site specific DNA binding domain; culturing the transformed cell in the presence of a ligand and determining expression of the reporter gene.

In another general aspect, the invention features a monoclonal antibody directed to RBAP-1. In preferred embodiments the monoclonal antibody is directed against a portion of RBAP-1 including the amino acid residues encoded by nucleotides 1191–1655 of RBAP-1 encoding DNA, as shown in FIG. 1.

In another general aspect the invention features eukaryotic homologues of RBAP-1. In preferred embodiments that eukaryotic homologues have been cloned using a portion of the RBAP-1 encoding DNA sequence as a probe.

DESCRIPTION OF THE PREFERRED EMBODIMENTS

Drawings

Figure 1A:
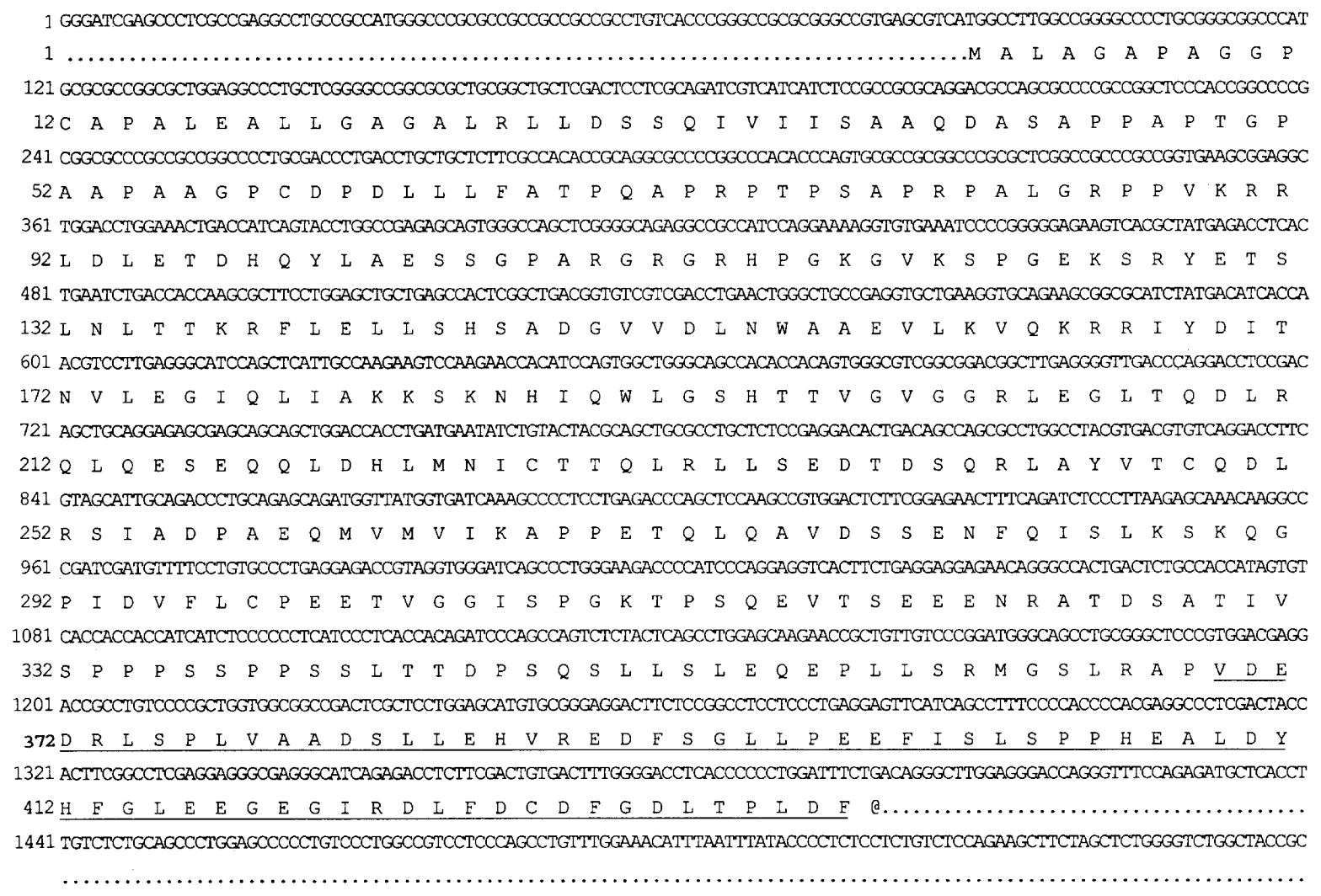

FIG. 1 is a diagram showing the nearly complete nucleic acid sequence of the RBAP-1 encoding DNA, and the deduced amino acid sequence. A candidate initiator methionine, M, is shown, although the sequence 5' of the corresponding ATG is open. The underlined sequence is the sequence of RBAP-1 that contains the RB pocket binding site.

CLONING AND CHARACTERIZATION OF RBAP-1

The following description, presented by way of example, details the cloning and characterization of RBAP-1. It will be appreciated that the genes of proteins that bind to RBAP-1 or the RBAP-1/RB protein complex can be cloned and characterized in an analogous manner.

The RBAP-1 encoding DNA was cloned from a λgt11 expression library using radiolabelled RB ("*RB") as a probe, according to cloning techniques generally known in the art (see for example, Singh et al., 1989, *Biotechniques*, Vol. 7, pp. 252–162). *RB was prepared using the pGEX-2TK plasmid described in U.S. patent application Ser. No. 736,847. Briefly, the library was plated at approximately 40,000 pfu/150 mm plate on 30 plates (pfu=plaque forming units). The expression of β-galactosidase fusion proteins was induced using IPTG impregnated nitrocellulose. The nitrocellulose was probed with *RB by incubating the nitrocellulose in a buffered solution containing *RB, and the unbound proteins were washed off. The plaques corresponding to the fusion proteins bound by *RB were picked and purified using further rounds of hybridization as is standard in the art. The DNA from the pure plaques was prepared and the sequence representing the RB-binding fusion protein was subcloned into pBKS (Stratagene) for sequencing. DNA sequencing was performed using a Sequenase 2.0 kit (available from United States Biochemical Corp.) according to a protocol provided by the manufacturer.

Analysis of the DNA sequence demonstrated that 4 of the clones contained overlapping DNA sequence and were derived from a common mRNA. Additional clones were obtained by screening another library and rescreening the original library with one of the above clones. The 2465 bp sequence of RBAP-1 was deduced from examination of multiple clones; the sequence shown in FIG. 1 is nearly the full length sequence of RBAP-1 encoding DNA, but may be missing about 500 bp from the 5' end, as determined by Northern Blot analysis.

The binding of the fusion proteins that comprise RBAP-1 to RB was characterized in vitro. Briefly, the purified λ phage of each fusion protein was plated on a separate plate, and the expression of the β-galactosidase fusion proteins was induced using IPTG impregnated nitrocellulose. The proteinis on the nitrocellulose were renatured (see Vinson et al., 1988, Genes & Dev., Vol. 2, pp. 801–806) and probed with *RB by incubating the nitrocellulose in a buffered solution containing *RB. The protein that were bound by *RB were visualized by autoradiography. The results of the autoradiograph demonstrated that all 4 fusion proteins of RBAP-1 were capable of binding directly to RB.

The ability of these proteins to bind to the RB pocket was determined by probing the nitrocellulose with a radiolabelled non-binding mutant of RB, and with *RB in the presence of a synthetic peptide homologous to the E7, E1A, T, viral transforming element. The results showed that the fusion proteins bound directly to the RB pocket and that the binding of these fusion proteins to RB could be significantly reduced or blocked by the viral transforming element.

Nucleotides 1191–1655 of the RBAP-1 encoding DNA, as shown in FIG. 1, were subdloned into pGEX-2T (see Kaelin et al., 1991), to create a glutathione S-transferase fusion protein ("GST-RBAP-1"), and used to determine whether RBAP-1 could bind to the phosphorylated or the underphosphorylated form of RB synthesized in vivo. Briefly, GST-RBAP-1 was purified from E. coli and bound to glutathione-Sepharose, RB was prepared from asynchronously growing cells and incubated with the Sepharose bound GST-RBAP-1. After washing, bound proteins were eluted from the Sepharose and immunoblotted with a monoclonal antibody against RB (monoclonal 245 available from Pharmigen). The results demonstrated that RBAP-1 specifically binds to the underphosphorylated form of RB.

The expression of the RBAP-1 gene was investigated using Northern analysis. The Northern analysis was performed using a RBAP-1 encoding DNA probe and total RNA obtained from peripheral blood T lymphocytes that were resting (G0 cells), blocked at the G1/S boundary, and synchronously growing. The results demonstrated that RBAP-1 mRNA accumulates when the cells are blocked at the G1/S boundary and falls after S phase.

The physical properties of RBAP-1 were examined using techniques that are well known in the art, and RBAP-1 was determined to have the same DNA-binding sequence specificity as E2F. Briefly, RBAP-1 co-purifies with E2F activity on DNA affinity columns (see, Means et al., 1992, Mol. Cel. Biol., Vol. 12, pp. 1054–1063). RBAP-1 immunoprecipitated from cell extracts using the monoclonal antibody against RBAP-1, described herein, and bacterially produced RBAP-1 were shown to contain E2F activity by nondenaturing polyacrylamide gel shift analysis using the E2F DNA-binding site for E2F (see, Shirodkar et al., 1992, Cell, Vol. 68, pp. 157–166). Additionally, RBAP-1 binds to the adenovirus E4 protein, a protein that is known to specifically bind to E2F, as was demonstrated by the binding of RBAP-1 to a GST-E4 fusion protein using the method described above (Kaelin et al., 1991).

The role of RBAP-1 in vivo

Without being limited thereby, we here propose a theory of a role of the RBAP-1 protein in vivo. We demonstrated that the RBAP-1 gene is expressed just prior to the point in the cell cycle that RB is phosphorylated, and that RBAP-1 binds specifically to the pocket of the underphosphorylated form of RB. Moreover, the RB pocket region is frequently mutated in human tumors and the underphosphorylated form of RB is thought to have tumor suppressing effects in that this form is believed to inhibit the progression of the cell cycle.

We propose two alternative models for the significance of RBAP-1 binding to RB. In one model, if RBAP-1 is present before the onset of RB phosphorylation, the binding of RBAP-1 to RB can lead to RB phosphorylation In this manner RBAP-1 would act "upstream" of RB in a signal transduction pathway and bring about the phosphorylation of RB. This model is consistent with the observation that loss of function RB mutants are hypophosphorylated in vivo, suggesting that cellular ligands of RB must bind to the RB pocket before phosphorylation can occur. Alternatively, RBAP-1 may be a "downstream" target of RB. In this model RBAP-1 binds to dephosphorylated RB generated near the end of M phase or is bound by newly synthesized RB that has not undergone post-translational modification.

Use

The invention provides for identification of ligands that bind to RBAP-1 or the RBAP-1/RB complex, identification of ligands that disrupt the binding of RB to a viral transforming protein, or the viral transforming element, and do not effect the binding of RB to RBAP-1, production of monoclonal antibodies directed to RBAP-1 or any peptide of RBAP-1, and detection of non-wild-type RBAP-1 genes or detection of alteration in the expression of wild-type RBAP-1 genes.

Identification of ligands that bind to RBAP-1 or RBAP-1/RB.

The RBAP-1 protein can be used to identify ligands that bind to or interact with RBAP-1 or with the RB/RBAP-1 complex. The identification of ligands that bind to RBAP-1 or the RBAP-1/RB complex can be approached using the same method by which RBAP-1 was cloned. For instance, labelled RBAP-1 or a complex of labelled RBAP-1/RB can be used as probes for expression libraries of fusion proteins, and the DNA encoding the protein that binds to either RBAP-1 or the RBAP-1/RB complex can be cloned generally as described above. Radioactive labelling is a preferred method for convenient labelling of proteins.

RBAP-1 or a complex of RBAP-1/RB can be used to screen a peptide library. The screening of a peptide library can be done using techniques generally known in the art (see for example Scott et al., 1990, Science, Vol. 249, pp. 386–390; Devlin et al., 1990, Science, Vol. 249, pp. 404–406; Lam et al., 1992, Nature, Vol.354, pp. 82–84). Briefly, RBAP-1 can be linked to a reporter gene, such as alkaline phosphatase ("AP") by cloning an in-frame fusion of RBAP-1 and AP ("AP/RBAP-1"), and used to screen a library of peptides linked to beads. The binding of AP/RBAP-1 to beads can be determined by staining and the amino acid sequence of the peptide on the bead determined by sequencing with a microsequencer (Lam et al.). In another approach, RBAP-1 can be attached to a solid support, such as a petri dish, and an epitope library, a peptide library inserted into a coat protein of filamentous phage such that the peptide is on the surface of the phage capsule, can be passed over the RBAP-1. Successive rounds of binding to RBAP-1 and propagating the phage that bind to RBAP-1 allows the purification of the individual phage clones (Scott et al.; Devlin et al.). The sequence of the peptide that binds to RBAP-1 can be determined by sequencing the DNA.

An in vitro assay for ligands, especially small molecules, that interact with RBAP-1 and alter its binding to DNA can be established, for example, by immobilizing RBAP-1 on a solid support, such as a microtiter tray well. The immobilized RBAP-1 can be incubated with a mixture of a ligand and a labelled DNA fragment, containing a sequence bound by the E2F activity. After incubation, the well can be washed to remove unbound species and the amount of label remaining in the well can be measured. A ligand that binds to RBAP-1 and disrupts the binding of RBAP-1 to the labelled DNA fragment can be detected by an absence of label remaining in the well.

Alternatively, an in vivo assay for ligands that bind to RBAP-1 and alter the activation of a gene that is transactivated by RBAP-1 can be established. For example this assay can be accomplished by transforming a cell, such as the yeast cell S. cerevisiae, with a reporter gene, such as β-galactosidase, under the control of an activatible promoter that has a sequence bound by the E2F activity upstream of the promoter. The cell is also transformed with a plasmid encoding RBAP-1. These cells can be grown in the presence of the chromogenic substrate X-gal, and the cells will produce a blue pigment if the β-galactosidase reporter gene is transactivated by RBAP-1 and transcribed. Cells can be cultured in the presence of different ligands and the ability of the ligand to disrupt the transactivation of the reporter gene can be measured by assaying for the disappearance of the blue color from cell colonies. Ligands that alter the activation of a gene by RBAP-1, either by decreasing the binding of RBAP-1 to the DNA or by decreasing the transactivation of the gene by RBAP-1 may be useful for therapeutic treatment of individuals that are lacking functional RB.

Identification of ligands that disrupt RB binding to viral transforming proteins without disrupting RB binding to RBAP-1.

RBAP-1 can be used to identify ligands that bind to RB and disrupt the binding of the viral transforming proteins to RB without affecting the binding of RBAP-1 to RB. The following methods for the identification of ligands are described for purposes of example only, and as will be appreciated methods within the invention may differ in particulars from those described.

An in vitro assay for ligands that disrupt the binding of RB and a viral RB binding protein, such as E7, E1A or T, can be established by immobilizing RB, RBAP-1 or a viral RB binding protein on a solid support, such as in a microtiter tray well. For example, RB can be immobilized on the solid support, and a mixture of a ligand and either labelled RBAP-1 ("*RBAP-1") or labelled E7 ("*E7") can be added to the wells of the microtiter plate. After incubation the wells can be washed to remove unbound species and the amount of label remaining in the well determined. A ligand that disrupts binding to RB can be detected by an absence of label remaining in the well. In particular, a ligand that specifically disrupts the binding of RB to E7 would be demonstrated by a lack of label remaining in the well where RB, *E7 and the ligand had been incubated together, and the presence of label in the well where RB, *RBAP-1, and the same ligand had been incubated. Radioactive labelling of the proteins is a preferred method for convenient labelling of proteins.

An in vivo assay for ligands can be established, for example, by using the yeast S. cerevisiae that contains a reporter gene, such as β-galactosidase, under the control of an activatible promoter, such as a promoter with multiple GAL4 binding sites. S. cerevisiae can be transformed with plasmids encoding chimeric proteins in which the DNA-binding region of GAL4 can be fused to RB ("GAL4-RB") and the transactivating region of VP16 can be fused to E7 ("VP16-E7") (see for example, Fields et al., 1989, Nature, Vol. 340, pp. 245–246; Dang et al., 1991, Mol. Cell. Biol., Vol. 11, pp. 954–962). These cells can be grown in the presence of the chromogenic substrate X-gal, and the cells produce a blue pigment if GAL4-RB fusion binds to the VP16-E7 fusion protein. The cells can be cultured in replicate in the presence of different ligands and the ability of the ligand to disrupt the binding of RB and E7 can be evidenced by an absence of blue pigment produced by the cells. In order to confirm a specific interaction between E7 and Rb, the ligand can be tested for its ability to disrupt the binding of RBAP-1 to RB using a VP16-RBAP-1 fusion protein in place of the VP16-E7 fusion protein in a similar assay.

An in vivo assay for ligands that disrupt the binding of RB and a viral transforming protein can alternatively be established in a mammalian cell in an analogous manner. For example a cervical carcinoma cell that expresses E7, such as HeLa cells, can be transformed with DNA-binding and transactivating fusion proteins of RB and RBAP-1, and a reporter gene downstream of an activatible promoter. These cells can be grown in the presence of different ligands in order to find a ligand that is capable of restoring the binding between RB and RBAP-1.

Ligands that appear to disrupt the binding of RB to the viral transforming element without disrupting the binding of RB to RBAP-1, can be assayed for the specificity of this disruption by determining their capacity to interfere with the binding of an unrelated pair of binding proteins. If the ligand is unable to disrupt the binding of other binding proteins then it can be concluded that the ligand interacts specifically with either RB or the viral transforming element to disrupt their binding.

A ligand that selectively disrupts RB binding to the viral transforming element may do so by binding to RB in such a way as to prevent the binding of the transforming element without disrupting the normal RB/RBAP-1 interaction, or may bind to the transforming element with a higher affinity than the affinity of RB and the transforming element. In either case such a ligand can be used in treatment of individuals suffering from a pathologic disease state, such as cervical carcinoma or a malignancy in which the RB signal transduction pathway has been disrupted.

Deletions of the RBAP-1 encoding DNA to define functional portions of the protein The RB pocket binding region of RBAP-1 can be further defined by constructing deletions of the RBAP-1 encoding DNA and determining binding of the proteins encoded by these deletion mutants to the RB pocket. Deletion mutations of RBAP-1 can be constructed from knowledge of the RBAP-1 sequence using techniques well known in the art. For example, a polymerase chain reaction technique can be used to construct a subclone of a specific portion of the DNA; or a series of deletion constructs, such as 3' deletions, can be constructed by cutting the DNA at a convenient restriction endonuclease site upstream of the stop codon and digesting the DNA with an exonuclease to produce a series of deletions in the 3' end of the DNA. Proteins encoded by deletion mutants of RBAP-1 can be assayed for their ability to specifically bind to the RB pocket as described above.

Monoclonal antibodies against RBAP-1

Monoclonal antibodies were raised against a peptide of RBAP-1 using techniques generally known in the art (Harlow et al., 1988, *Antibodies, A Laboratory Manual*, Cold Spring Harbor Laboratory, Chapter 6). As will be understood, a monoclonal antibody against any portion of RBAP-1 can be produced using the techniques described below, or any of the techniques described by Harlow et al.

Briefly, the GST-RBAP-1 fusion protein described above, that is composed of nucleotides 1191–1655 of FIG. 1 fused to glutathione S-transferase, was overexpressed in E. coli and isolated. The fusion protein as suspended in complete Freund's adjuvant and injected intraperitoneally into mice. Each mouse was boosted with the isolated fusion protein in incomplete Freund's adjuvant by another intraperitoneal injection approximately two weeks later, and serum was collected from the mouse by tail bleed an additional 10 or more days later. The serum was tested for antibodies against RBAP-1, and subsequent rounds of boosting and bleeding were done as necessary. Serum samples were checked for specific recognition of RBAP-1 by immunoprecipitation of radiolabelled RBAP-1 and the mice which had produced the best response were prepared for hybridoma fusion. The final booster injection was given 3 weeks after the latest boost, and about 3 days prior to hybridoma fusion, the booster was delivered both as an intravenous injection and an intraperitoneal injection. The spleen was removed from the immunized mice and the cells were separated. The spleen cells were fused to myeloma cells with polyethylene glycol, and the fused cells were aliquoted into wells of a microtiter plate. The cells were grown in selective medium to select for the growth of hybridoma cells only. The wells containing colonies of hybridomas were screened by removing a portion of the cell culture supernatant and detecting the secretion of antibodies by antibody capture on permeabilized cells or in solution. The specific hybridoma colony that secretes antibody was cloned by limiting dilution and expanded by growing in successively larger containers.

Detection of non-wild-type RBAP-1 or alterations in expression of wild-type RBAP-1

The detection of alterations of expression of wild-type RBAP-1 or the presence of non-wild-type RBAP-1 in a tissue sample from a subject, using techniques well known in the art, can provide for early diagnosis of a neoplasm. The following methods are presented for purposes of example only, the methods employed can differ from the described methods and remain within the spirit of the invention.

Alterations in the level of RBAP-1 expression can be detected by a well known technique such as Northern blotting of the RBAP-1 mRNA.

Mutations in the RBAP-1 gene, including point mutations and specific deletions or insertions of the coding sequence, the 5' untranslated region and the 3' untranslated region, can be detected by cloning and sequencing the RBAP-1 allele present in the sample taken from the subject. If desired, the RBAP-1 mRNA can be sequenced directly, or the polymerase chain reaction technique ("PCR") can be used to amplify RBAP-1 or its mRNA to produce encoding DNA ("cDNA") and the resultant cDNA can be sequenced. PCR can also be used to selectively amplify a region of the RBAP-1 allele; this can be especially useful to identify mutations at the splice-donor sites and in the 3' and 5' untranslated regions.

Mutations in the RBAP-1 gene can alternatively be detected using single strand conformation polymorphisms (Orita et al., 1989, Proc. Natl. Acad. Sci., USA, Vol. 86, pp. 2766–2770). This technique detects deletions and is sensitive enough to detect nucleotide substitutions. For the analysis, RBAP-1 can be cloned from a sample taken from the subject, or the genomic DNA can be prepared from the sample and either amplified using the polymerase chain reaction technique ("PCR") or directly digested with a restriction endonuclease. If the DNA sample is cloned or prepared by PCR then the sample can be radiolabelled, denatured, and subjected to neutral polyacrylamide gel electrophoresis. The gel can be dried and exposed to film to determine any differences in mobility between the sample from the patient and the wild-type RBAP-1 control sample. If the DNA sample is prepared by digestion of genomic DNA, it is denatured, subjected to neutral polyacrylamide gel electrophoresis, and the single-stranded DNA's are transferred to nitrocellulose or nylon membrane. The transferred DNA's are probed with radiolabelled RBAP-1 and any differences in mobility between the DNA from the sample and the wild-type RBAP-1 control can be visualized by an autoradiographic exposure of the DNA's.

Mutations in the RBAP-1 gene can also be detected using a nucleic acid probe that is complementary to a portion of RBAP-1. This technique is traditionally used to detect point mutations, and one can use a riboprobe (sense or antisense) which is complementary to the wild-type RBAP-1 gene sequence to detect point mutations in the coding DNA. The riboprobe is first annealed to either mRNA or DNA isolated from the tissue sample, then cleaved with ribonuclease to specifically cleave the riboprobe at mismatches between it and the sample. The cleaved products are separated by gel electrophoresis, and mismatches are detected as segments of the riboprobe smaller than the fill length riboprobe. The point mutations can also be detected using a DNA probe. Mutations in the RBAP-1 gene that have previously been identified can be detected using allele-specific probes containing a gene sequence corresponding to that mutation. Presence of a specific mutation is confirmed when an allele-specific probe hybridizes with RBAP-1 sequences from the sample.

Cloning of the genomic RBAP-1 DNA

The RBAP-1 gene can be cloned, for example, by first screening Southern blots of restriction endonuclease digests of genomic DNA from normal peripheral blood lymphocytes with labelled RBAP-1 encoding DNA to determine the size of the RBAP-1 gene and determine an appropriate cosmid library with which to pursue the cloning of the gene. The cosmid library can then be screened using conventional techniques with labelled RBAP-1 encoding DNA and the RBAP-1 gene can be subdloned into an appropriate plasmid vector, such as pBluescript, and sequenced.

Cloning of eukaryotic homologues to RBAP-1

The RBAP-1 encoding DNA ("cDNA") can be used to select probes to clone the cDNA or genomic DNA that encodes the RBAP-1 homologue in other eukaryotic species. A "homologue", as that term is used herein, means a protein in another eukaryotic species that has the same functional properties as the RBAP-1 protein in humans. Techniques for cloning homologues to a known gene are generally known in the art. For example, a Southern blot of DNA from a desired eukaryote can be screened at low stringency using a labelled portion of RBAP-1 probe or a labelled oligodeoxynucleotide, that was chosen based upon the RBAP-1 sequence, as a probe, and the RBAP-1 homologue can be cloned using an appropriate DNA library from the eukaryote (see for example, Sambrook et al., 1989, Molecular Cloning: A Laboratory Manual, 2nd Ed., Cold Spring Harbor Laboratory Press). In another technique the sequence of the RBAP-1 cDNA can be used to design degenerate oligodeoxynucleotide primers, and a polymerase chain reaction can be conducted using the degenerate primers and DNA from a desired eukaryote (see for example, Hanks et al., 1987, Proc. Natl. Acad. Sci., USA, Vol. 84, pp. 388–392; Lee et al., 1988, Science, Vol. 239, pp. 1288–1291).

Other embodiments are within the following claims.

We claim:

1. An isolated DNA segment that binds under low stringency to a labeled portion of an E2F1 DNA of SEQ ID NO: 1 in which the complimentary strand of the DNA segment encodes a polypeptide that (a) co-purifies with E2F activity on a DNA affinity column;
(b) binds to adenovirus E4 protein; and
(c) binds to the pocket region of the underphosphorylated form of the retinoblastoma gene product.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2456 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GGGATCGAGC CCTCGCCGAG GCCTGCCGCC ATGGGCCCGC GCCGCCGCCG CCGCCTGTCA      60

CCCGGGCCGC GCGGGCCGTG AGCGTCATGG CCTTGGCCGG GGCCCCTGCG GGCGGCCCAT     120

GCGCGCCGGC GCTGGAGGCC CTGCTCGGGG CCGGCGCGCT GCGGCTGCTC GACTCCTCGC     180

AGATCGTCAT CATCTCCGCC GCGCAGGACG CCAGCGCCCC GCCGGCTCCC ACCGGCCCCG     240

CGGCGCCCGC CGCCGGCCCC TGCGACCCTG ACCTGCTGCT CTTCGCCACA CCGCAGGCGC     300

CCCGGCCCAC ACCCAGTGCG CCGCGGCCCG CGCTCGGCCG CCCGCCGGTG AAGCGGAGGC     360

TGGACCTGGA AACTGACCAT CAGTACCTGG CCGAGAGCAG TGGGCCAGCT CGGGGCAGAG     420

GCCGCCATCC AGGAAAAGGT GTGAAATCCC CGGGGGAGAA GTCACGCTAT GAGACCTCAC     480

TGAATCTGAC CACCAAGCGC TTCCTGGAGC TGCTGAGCCA CTCGGCTGAC GGTGTCGTCG     540

ACCTGAACTG GGCTGCCGAG GTGCTGAAGG TGCAGAAGCG GCGCATCTAT GACATCACCA     600

ACGTCCTTGA GGGCATCCAG CTCATTGCCA AGAAGTCCAA GAACCACATC CAGTGGCTGG     660

GCAGCCACAC CACAGTGGGC GTCGGCGGAC GGCTTGAGGG GTTGACCCAG GACCTCCGAC     720

AGCTGCAGGA GAGCGAGCAG CAGCTGGACC ACCTGATGAA TATCTGTACT ACGCAGCTGC     780

GCCTGCTCTC CGAGGACACT GACAGCCAGC GCCTGGCCTA CGTGACGTGT CAGGACCTTC     840

GTAGCATTGC AGACCCTGCA GAGCAGATGG TTATGGTGAT CAAAGCCCCT CCTGAGACCC     900

AGCTCCAAGC CGTGGACTCT TCGGAGAACT TTCAGATCTC CCTTAAGAGC AAACAAGGCC     960

CGATCGATGT TTTCCTGTGC CCTGAGGAGA CCGTAGGTGG GATCAGCCCT GGGAAGACCC    1020

CATCCCAGGA GGTCACTTCT GAGGAGGAGA ACAGGGCCAC TGACTCTGCC ACCATAGTGT    1080

CACCACCACC ATCATCTCCC CCCTCATCCC TCACCACAGA TCCCAGCCAG TCTCTACTCA    1140

GCCTGGAGCA AGAACCGCTG TTGTCCCGGA TGGGCAGCCT GCGGGCTCCC GTGGACGAGG    1200

ACCGCCTGTC CCCGCTGGTG GCGGCCGACT CGCTCCTGGA GCATGTGCGG GAGGACTTCT    1260

CCGGCCTCCT CCCTGAGGAG TTCATCAGCC TTTCCCCACC CCACGAGGCC CTCGACTACC    1320

ACTTCGGCCT CGAGGAGGGC GAGGGCATCA GAGACCTCTT CGACTGTGAC TTTGGGGACC    1380

TCACCCCCCT GGATTTCTGA CAGGGCTTGG AGGGACCAGG GTTTCCAGAG ATGCTCACCT    1440

TGTCTCTGCA GCCCTGGAGC CCCCTGTCCC TGGCCGTCCT CCCAGCCTGT TTGGAAACAT    1500

TTAATTTATA CCCCTCTCCT CTGTCTCCAG AAGCTTCTAG CTCTGGGGTC TGGCTACCGC    1560

TAGGAGGCTG AGCAAGCCAG GAAGGGAAGG AGTCTGTGTG GTGTGTATGT GCATGCAGCC    1620

TACACCCACA CGTGTGTACC GGGGGTGAAT GTGTGTGAGC ATGTGTGTGT GCATGTACCG    1680
```

```
GGGAATGAAG GTGAACATAC ACCTCTGTGT GTGCACTGCA GACACGCCCC AGTGTGTCCA      1740

CATGTGTGTG CATGAGTCCA TGTGTGCGCG TGGGGGGGCT CTAACTGCAC TTTCGGCCCT      1800

TTTGCTCTGG GGGTCCACAA GGCCCAGGGC AGTGCCTGCT CCCAGAATCT GGTGCTCTGA      1860

CCAGGCCAGG TGGGGAGGCT TTGGCTGGCT GGGCGTGTAG GACGGTGAGA GCACTTCTGT      1920

CTTAAAGGTT TTTTCTGATT GAAGCTTTAA TGGAGCGTTA TTTATTTATC GAGGCCTCTT      1980

TGGTGAGCCT GGGGAATCAG CAAAGGGGAG GAGGGGTGTG GGGTTGATAC CCCAACTCCC      2040

TCTACCCTTG AGCAAGGGCA GGGGTCCCTG AGCTGTTCTT CTGCCCCATA CTGAAGGAAC      2100

TGAGGCCTGG GTGATTTATT TATTGGGAAA GTGAGGGAGG GAGACAGACT GACTGACAGC      2160

CATGGGTGGT CAGATGGTGG GGTGGGCCCT CTCCAGGGGG CCAGTTCAGG GCCCCAGCTG      2220

CCCCCCAGGA TGGATATGAG ATGGGAGAGG TGAGTGGGGG ACCTTCACTG ATGTGGGCAG      2280

GAGGGGTGGT GAAGGCCTCC CCCAGCCCAG ACCCTGTGGT CCCTCCTGCA GTGTCTGAAG      2340

CGCCTGCCTC CCCACTGCTC TGCCCCACCC TCCAATCTGC ACTTTGATTT GCTTCCTAAC      2400

AGCTCTGTTC CCTCCTGCTT TGGTTTTAAT AAATATTTTG ATGACGTTAA AAAAAA         2456

(2) INFORMATION FOR SEQ ID NO:2:

(i) SEQUENCE CHARACTERISTICS:
            (A) LENGTH: 437 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:2:

Met Ala Leu Ala Gly Ala Pro Ala Gly Gly Pro Cys Ala Pro Ala Leu
1               5                   10                  15

Glu Ala Leu Leu Gly Ala Gly Ala Leu Arg Leu Leu Asp Ser Ser Gln
            20                  25                  30

Ile Val Ile Ile Ser Ala Ala Gln Asp Ala Ser Ala Pro Pro Ala Pro
        35                  40                  45

Thr Gly Pro Ala Ala Pro Ala Ala Gly Pro Cys Asp Pro Asp Leu Leu
    50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
            100                 105                 110

Arg His Pro Gly Lys Gly Val Lys Ser Pro Gly Glu Lys Ser Arg Tyr
        115                 120                 125

Glu Thr Ser Leu Asn Leu Thr Thr Lys Arg Phe Leu Glu Leu Leu Ser
    130                 135                 140

His Ser Ala Gly Asp Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
            180                 185                 190

Ser His Thr Thr Val Gly Val Gly Gly Arg Leu Glu Gly Leu Thr Gln
        195                 200                 205

Asp Leu Arg Gln Leu Gln Glu Ser Glu Gln Gln Leu Asp His Leu Met
```

-continued

```
            210                 215                 220
Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
                260                 265                 270

Leu Gln Ala Val Asp Ser Ser Glu Asn Phe Gln Ile Ser Leu Lys Ser
                275                 280                 285

Lys Gln Gly Pro Ile Asp Val Phe Leu Cys Pro Glu Glu Thr Val Gly
                290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Pro Ser
                325                 330                 335

Ser Pro Pro Ser Ser Leu Thr Thr Asp Pro Ser Gln Ser Leu Leu Ser
                340                 345                 350

Leu Glu Gln Glu Pro Leu Leu Ser Arg Met Gly Ser Leu Arg Ala Pro
                355                 360                 365

Val Asp Glu Asp Arg Leu Ser Pro Leu Val Ala Ala Asp Ser Leu Leu
                370                 375                 380

Glu His Val Arg Glu Asp Phe Ser Gly Leu Leu Pro Glu Glu Phe Ile
385                 390                 395                 400

Ser Leu Ser Pro Pro His Glu Ala Leu Asp Tyr His Phe Gly Leu Glu
                405                 410                 415

Glu Gly Glu Gly Ile Arg Asp Leu Phe Asp Cys Asp Phe Gly Asp Leu
                420                 425                 430

Thr Pro Leu Asp Phe
                435
```